(12) United States Patent
Govea et al.

(10) Patent No.: US 10,232,169 B2
(45) Date of Patent: Mar. 19, 2019

(54) BURR HOLE PLUGS FOR ELECTRICAL STIMULATION SYSTEMS AND METHODS OF MAKING AND USING

(71) Applicant: Boston Scientific Neuromodulation Corporation, Valencia, CA (US)

(72) Inventors: Michael X. Govea, Glendale, CA (US); Joshua Dale Howard, Sacramento, CA (US); David Ernest Wechter, San Francisco, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 361 days.

(21) Appl. No.: 15/217,844

(22) Filed: Jul. 22, 2016

(65) Prior Publication Data

US 2017/0021162 A1 Jan. 26, 2017

Related U.S. Application Data

(60) Provisional application No. 62/196,184, filed on Jul. 23, 2015.

(51) Int. Cl.
*A61N 1/05* (2006.01)
*A61N 1/375* (2006.01)

(52) U.S. Cl.
CPC .......... *A61N 1/0539* (2013.01); *A61N 1/0534* (2013.01); *A61N 1/375* (2013.01)

(58) Field of Classification Search
CPC .................................................. A61N 1/0539
See application file for complete search history.

(56) References Cited

U.S. PATENT DOCUMENTS

| 979,652 A | 12/1910 | Church |
| 2,186,277 A | 1/1940 | Tetens |

(Continued)

FOREIGN PATENT DOCUMENTS

| EP | 0911061 | 4/1999 |
| JP | S55-112538 | 7/1980 |

(Continued)

OTHER PUBLICATIONS

Pianca, et al. inventors for AB-184U; U.S. Appl. No. 10/052,331, filed Jan. 18, 2002; entitled "Cranial Sealing Plug", 36 pages.

(Continued)

*Primary Examiner* — Carl H Layno
*Assistant Examiner* — Jennifer L Ghand
(74) *Attorney, Agent, or Firm* — Lowe Graham Jones PLLC; Bruce E. Black

(57) ABSTRACT

A burr hole plug includes a first plug base defining a burr hole aperture and including first grooves; a second plug base to be disposed around the first plug base and including second grooves to receive a portion of an electrical stimulation lead; a cover to be disposed on the second plug base; a cap to be disposed over the burr hole aperture and coupled to the first plug base; and an extension coupled to, and extending away from, the cover. The extension includes conductors and the second plug base and the cover include conductive elements to electrically couple the terminals of the electrical stimulation lead, when disposed in the second grooves, to the conductors of the extension. An alternative burr hole plug includes a lead connector disposed on the cap and having a connector aperture to receive the proximal end of the electrical stimulation lead.

20 Claims, 13 Drawing Sheets

(56) References Cited

U.S. PATENT DOCUMENTS

| | | |
|---|---|---|
| 2,521,301 A | 9/1950 | Morrison |
| 2,873,822 A | 2/1959 | Sloan |
| 2,912,712 A | 11/1959 | Shamban et al. |
| 3,758,827 A | 9/1973 | Schroder et al. |
| 3,826,952 A | 7/1974 | Iwasaki et al. |
| 3,829,737 A | 8/1974 | Johnsson |
| 4,114,603 A | 9/1978 | Wilkinson |
| 4,245,645 A | 1/1981 | Arseneault et al. |
| 4,297,609 A | 10/1981 | Hirao et al. |
| 4,315,180 A | 2/1982 | Kondo et al. |
| 4,328,313 A | 5/1982 | Simonson et al. |
| 4,328,813 A | 5/1982 | Ray |
| 4,467,800 A | 8/1984 | Zytkovicz |
| 4,741,571 A | 5/1988 | Godette |
| 4,805,634 A | 2/1989 | Ullrich et al. |
| 4,826,487 A | 5/1989 | Winter |
| 4,850,359 A | 7/1989 | Putz |
| 4,931,056 A | 6/1990 | Ghajar et al. |
| 4,955,891 A | 9/1990 | Carol |
| 4,998,938 A | 3/1991 | Ghajar et al. |
| 5,116,345 A | 5/1992 | Jewell et al. |
| 5,201,737 A | 4/1993 | Leibinger et al. |
| 5,235,990 A | 8/1993 | Dempsey |
| 5,300,080 A | 4/1994 | Clayman et al. |
| 5,330,485 A | 7/1994 | Clayman et al. |
| 5,464,446 A | 11/1995 | Dreessen et al. |
| 5,484,445 A | 1/1996 | Knuth |
| 5,496,356 A | 3/1996 | Hudz |
| 5,503,164 A | 4/1996 | Friedman |
| 5,549,620 A | 8/1996 | Bremer |
| 5,707,373 A | 1/1998 | Sevrain et al. |
| 5,732,699 A | 3/1998 | Lundback |
| 5,776,144 A | 7/1998 | Levsieffer et al. |
| 5,800,504 A | 9/1998 | Bellifemine |
| 5,843,150 A | 12/1998 | Dreessen et al. |
| 5,865,842 A | 2/1999 | Knuth et al. |
| 5,891,028 A | 4/1999 | Lundback |
| 5,897,531 A | 4/1999 | Amirana |
| 5,916,154 A | 6/1999 | Hobbs et al. |
| 5,927,277 A | 7/1999 | Baudino et al. |
| 5,954,687 A | 9/1999 | Baudino |
| 5,984,930 A | 11/1999 | Maciunas et al. |
| 5,993,463 A | 11/1999 | Truwit |
| 6,006,124 A | 12/1999 | Fischell et al. |
| 6,016,449 A | 1/2000 | Fischell et al. |
| 6,044,304 A | 3/2000 | Baudino |
| 6,050,098 A | 4/2000 | Meyer et al. |
| 6,050,998 A | 4/2000 | Fletcher |
| 6,073,048 A | 6/2000 | Kieval et al. |
| 6,094,598 A | 7/2000 | Elsberry et al. |
| 6,117,143 A | 9/2000 | Hynes et al. |
| 6,126,663 A | 10/2000 | Hair |
| 6,128,537 A | 10/2000 | Rise |
| 6,128,538 A | 10/2000 | Fischell et al. |
| 6,134,474 A | 10/2000 | Fischell et al. |
| 6,134,477 A | 10/2000 | Knuteson |
| 6,171,239 B1 | 1/2001 | Humphrey |
| 6,175,710 B1 | 1/2001 | Kamaji et al. |
| 6,181,969 B1 | 1/2001 | Gord |
| 6,200,329 B1 | 3/2001 | Fung et al. |
| 6,210,417 B1 | 4/2001 | Baudino et al. |
| 6,224,450 B1 | 5/2001 | Norton |
| 6,230,049 B1 | 5/2001 | Fischell et al. |
| 6,269,270 B1 | 7/2001 | Boveja |
| 6,271,094 B1 | 8/2001 | Boyd et al. |
| 6,284,729 B1 | 9/2001 | Bernfield et al. |
| 6,295,944 B1 | 10/2001 | Lovett |
| 6,321,104 B1 | 11/2001 | Gielen et al. |
| 6,324,433 B1 | 11/2001 | Errico |
| 6,353,762 B1 | 3/2002 | Baudino et al. |
| 6,354,299 B1 | 3/2002 | Fischell et al. |
| 6,356,729 B1 | 3/2002 | Sasaki et al. |
| 6,356,777 B1 | 3/2002 | Garfield et al. |
| 6,356,792 B1 | 3/2002 | Errico |
| 6,364,278 B1 | 4/2002 | Lin et al. |
| 6,374,140 B1 | 4/2002 | Rise |
| 6,391,985 B1 | 5/2002 | Goode et al. |
| 6,413,263 B1 | 7/2002 | Lobdill et al. |
| 6,427,086 B1 | 7/2002 | Fischell et al. |
| 6,447,443 B1 | 9/2002 | Keogh et al. |
| 6,459,936 B2 | 10/2002 | Fischell et al. |
| 6,463,328 B1 | 10/2002 | John |
| 6,464,687 B1 | 10/2002 | Ishikawa et al. |
| 6,466,822 B1 | 10/2002 | Pless |
| 6,480,743 B1 | 11/2002 | Kirkpatrick et al. |
| 6,482,182 B1 | 11/2002 | Carroll et al. |
| 6,516,227 B1 | 2/2003 | Meadows |
| 6,560,486 B1 | 5/2003 | Osorio et al. |
| 6,571,127 B1 | 5/2003 | Ben-Haim et al. |
| 6,574,498 B1 | 6/2003 | Gilboa |
| 6,597,954 B1 | 7/2003 | Pless et al. |
| 6,609,020 B2 | 8/2003 | Gill |
| 6,609,029 B1 | 8/2003 | Mann et al. |
| 6,609,032 B1 | 8/2003 | Woods et al. |
| 6,618,623 B1 | 9/2003 | Pless et al. |
| 6,647,296 B2 | 11/2003 | Fischell et al. |
| 6,690,974 B2 | 2/2004 | Archer et al. |
| 6,741,892 B1 | 5/2004 | Meadows et al. |
| 6,795,737 B2 | 9/2004 | Gielen et al. |
| 6,845,257 B2 | 1/2005 | Fuimaono et al. |
| 6,845,267 B2 | 1/2005 | Harrison et al. |
| 6,920,359 B2 | 7/2005 | Meadows et al. |
| 6,944,501 B1 | 9/2005 | Pless |
| 6,950,707 B2 | 9/2005 | Whitehurst |
| 7,004,948 B1 | 2/2006 | Pianca et al. |
| 7,033,326 B1 | 4/2006 | Pianca et al. |
| 7,050,855 B2 | 5/2006 | Zeijlemaker et al. |
| 7,090,661 B2 | 8/2006 | Morris et al. |
| 7,146,222 B2 | 12/2006 | Boling |
| 7,174,213 B2 | 2/2007 | Pless |
| 7,174,219 B2 | 2/2007 | Wahlstrand et al. |
| 7,177,701 B1 | 2/2007 | Pianca |
| 7,204,840 B2 | 4/2007 | Skakoon et al. |
| 7,235,084 B2 | 6/2007 | Skakoon et al. |
| 7,244,150 B1 | 7/2007 | Brase et al. |
| 7,343,205 B1 | 3/2008 | Pianca et al. |
| 7,369,899 B2 | 5/2008 | Malinowski et al. |
| 7,421,297 B2 | 9/2008 | Gifakis et al. |
| 7,437,193 B2 | 10/2008 | Parramon et al. |
| 7,450,997 B1 | 11/2008 | Pianca et al. |
| 7,454,251 B2 | 11/2008 | Rezai et al. |
| 7,479,146 B2 | 1/2009 | Malinowski et al. |
| 7,548,775 B2 | 6/2009 | Kipke et al. |
| 7,636,596 B2 | 12/2009 | Solar |
| 7,672,734 B2 | 3/2010 | Anderson et al. |
| 7,756,922 B2 | 7/2010 | Basu et al. |
| 7,761,165 B1 | 7/2010 | He et al. |
| 7,766,922 B1 | 8/2010 | Daglow et al. |
| 7,783,359 B2 | 8/2010 | Meadows |
| 7,787,945 B2 | 8/2010 | Greene |
| 7,792,590 B1 | 9/2010 | Pianca et al. |
| 7,809,446 B2 | 10/2010 | Meadows |
| 7,815,651 B2 | 10/2010 | Skakoon et al. |
| 7,833,231 B2 | 11/2010 | Skakoon et al. |
| 7,833,253 B2 | 11/2010 | Ralph et al. |
| 7,949,395 B2 | 5/2011 | Kuzma |
| 7,974,706 B2 | 7/2011 | Moffitt et al. |
| 8,224,450 B2 | 7/2012 | Brase |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0052610 A1 | 5/2002 | Skakoon et al. |
| 2002/0072770 A1 | 6/2002 | Pless |
| 2002/0077670 A1 | 6/2002 | Archer et al. |
| 2002/0099412 A1 | 7/2002 | Fischell et al. |
| 2002/0156372 A1 | 10/2002 | Skakoon et al. |
| 2002/0169485 A1 | 11/2002 | Pless et al. |
| 2003/0028199 A1 | 2/2003 | Ghahremani et al. |
| 2003/0083724 A1 | 5/2003 | jog et al. |
| 2003/0088274 A1 | 5/2003 | Gliner et al. |
| 2003/0088303 A1 | 5/2003 | Goode |
| 2004/0034367 A1 | 2/2004 | Malinowski |
| 2004/0122446 A1 | 6/2004 | Solar |
| 2004/0153129 A1 | 8/2004 | Pless et al. |

(56) References Cited

U.S. PATENT DOCUMENTS

| | | |
|---|---|---|
| 2004/0176673 A1 | 9/2004 | Wahlstrand et al. |
| 2005/0010261 A1 | 1/2005 | Luders et al. |
| 2005/0015128 A1 | 1/2005 | Rezai et al. |
| 2005/0049646 A1 | 3/2005 | Luders et al. |
| 2005/0070458 A1 | 3/2005 | John |
| 2005/0075679 A1 | 4/2005 | Gliner et al. |
| 2005/0075680 A1 | 4/2005 | Lowry et al. |
| 2005/0092707 A1 | 5/2005 | Chantalat |
| 2005/0107753 A1 | 5/2005 | Rezai et al. |
| 2005/0182421 A1 | 8/2005 | Schulte et al. |
| 2005/0182422 A1 | 8/2005 | Schulte et al. |
| 2005/0182423 A1 | 8/2005 | Schulte et al. |
| 2005/0182424 A1 | 8/2005 | Schulte et al. |
| 2005/0182425 A1 | 8/2005 | Schulte et al. |
| 2005/0182464 A1 | 8/2005 | Schulte et al. |
| 2005/0222641 A1 | 10/2005 | Pless |
| 2005/0228249 A1 | 10/2005 | Boling |
| 2006/0129204 A1 | 6/2006 | Pless et al. |
| 2006/0190054 A1 | 8/2006 | Malinowski et al. |
| 2006/0190055 A1 | 8/2006 | Malinowski et al. |
| 2006/0212093 A1 | 9/2006 | Pless et al. |
| 2006/0224216 A1 | 10/2006 | Pless et al. |
| 2006/0229686 A1 | 10/2006 | Giftakis et al. |
| 2006/0247684 A1 | 11/2006 | Halperin et al. |
| 2007/0106143 A1 | 5/2007 | Flaherty |
| 2007/0150036 A1 | 6/2007 | Anderson |
| 2007/0173844 A1 | 7/2007 | Ralph et al. |
| 2007/0208352 A1 | 9/2007 | Henderson et al. |
| 2007/0225773 A1 | 9/2007 | Shen et al. |
| 2007/0233158 A1 | 10/2007 | Rodriguez |
| 2007/0265683 A1 | 11/2007 | Ehrlich |
| 2008/0071313 A1 | 3/2008 | Stevenson et al. |
| 2008/0100061 A1 | 5/2008 | Sage et al. |
| 2008/0172068 A1 | 7/2008 | Adams et al. |
| 2008/0243219 A1 | 10/2008 | Malinowski et al. |
| 2008/0275466 A1 | 11/2008 | Skakoon |
| 2009/0112327 A1 | 4/2009 | Lane et al. |
| 2009/0118804 A1 | 5/2009 | Moffitt et al. |
| 2009/0157157 A1 | 6/2009 | Schorn et al. |
| 2009/0182351 A1 | 7/2009 | Malinowski et al. |
| 2009/0187149 A1 | 7/2009 | Nelson |
| 2009/0187222 A1 | 7/2009 | Barker |
| 2009/0276021 A1 | 11/2009 | Meadows et al. |
| 2010/0023020 A1 | 1/2010 | Barker et al. |
| 2010/0023100 A1 | 1/2010 | Barker |
| 2010/0076535 A1 | 3/2010 | Pianca et al. |
| 2010/0145357 A1 | 6/2010 | Lane et al. |
| 2010/0268298 A1 | 10/2010 | Moffitt et al. |
| 2010/0280585 A1* | 11/2010 | Appenrodt ............ A61N 1/0529 607/149 |
| 2010/0312193 A1* | 12/2010 | Stratton ................ A61M 39/02 604/175 |
| 2011/0004267 A1 | 1/2011 | Meadows |
| 2011/0005069 A1 | 1/2011 | Pianca |
| 2011/0078900 A1 | 4/2011 | Pianca et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0316615 A1 | 12/2012 | Digiore et al. |
| 2013/0006410 A1 | 1/2013 | Gentile et al. |
| 2013/0066430 A1 | 3/2013 | Funderburk |
| 2013/0066431 A1 | 3/2013 | Funderburk |
| 2013/0105071 A1 | 5/2013 | Digiore et al. |
| 2014/0257325 A1* | 9/2014 | Chavez ................ A61N 1/0539 606/129 |
| 2015/0045864 A1 | 2/2015 | Howard |

FOREIGN PATENT DOCUMENTS

| | | |
|---|---|---|
| WO | 1998008554 | 3/1998 |
| WO | 1999055408 | 11/1999 |
| WO | 2000013743 | 3/2000 |
| WO | 20020045795 | 6/2002 |
| WO | 2003026738 | 4/2003 |
| WO | 20030028521 | 4/2003 |
| WO | 20040084749 | 10/2004 |
| WO | 2004105640 | 12/2004 |
| WO | 2005079903 | 9/2005 |
| WO | 2006031317 | 3/2006 |
| WO | 2008054691 | 5/2008 |
| WO | 2008054699 | 5/2008 |
| WO | 2008107815 | 9/2008 |
| WO | 2008107822 | 9/2008 |
| WO | 2008134509 | 11/2008 |
| WO | 2009055746 | 4/2009 |

OTHER PUBLICATIONS

Roberts DW, Hartov A. Kennedy FE, Miga MI, Paulsen KD: Intraoperative brain shift and deformation: A quantitative analysis of cortical displacement in 28 cases. Neurosurgery 43:749-760, 1998.

Dickhaus H., Ganser KA, Stuabert A., Bonsanto MM, Wirtz CR, Tronnier VM, Kunze S: Quantification of brain shift effects by MR-imaging. Engineering in Medicine and Biology Society vol. 2: 491-494, 1997.

Nimsky C., Gansland 0., Cerny S., Hastreiter P, Greiner G., Fahlbusch R.: Quantification of, visualization of, and compensation for brain shift using intraoperative magnetic resonance imaging. Neurosurgery 47, 1070-1080, 2000.

Winkler D., Tittgemeyer M., Schwartz J., Preul C., Strecker K., Meixensberger J.: The first evaluation of brain shift during functional neurosurgery by deformation field analysis. Journal of Neurology, Neurosurgery, and Psychiatry 76 (8): 1161-3, 2005.

Axelsson, Stefan et al., Longitudinal cephalometric standards for the neurocranium in Norwegians from 6 to 21 years of age, European Journal of Orthodontics, vol. 25 (2003) pp. 185-198.

Lieberman, Daniel E. et al., Basicranial influence on overall cranial shape, Journal of Human Evolution, vol. 38 (2000) pp. 291-315.

\* cited by examiner

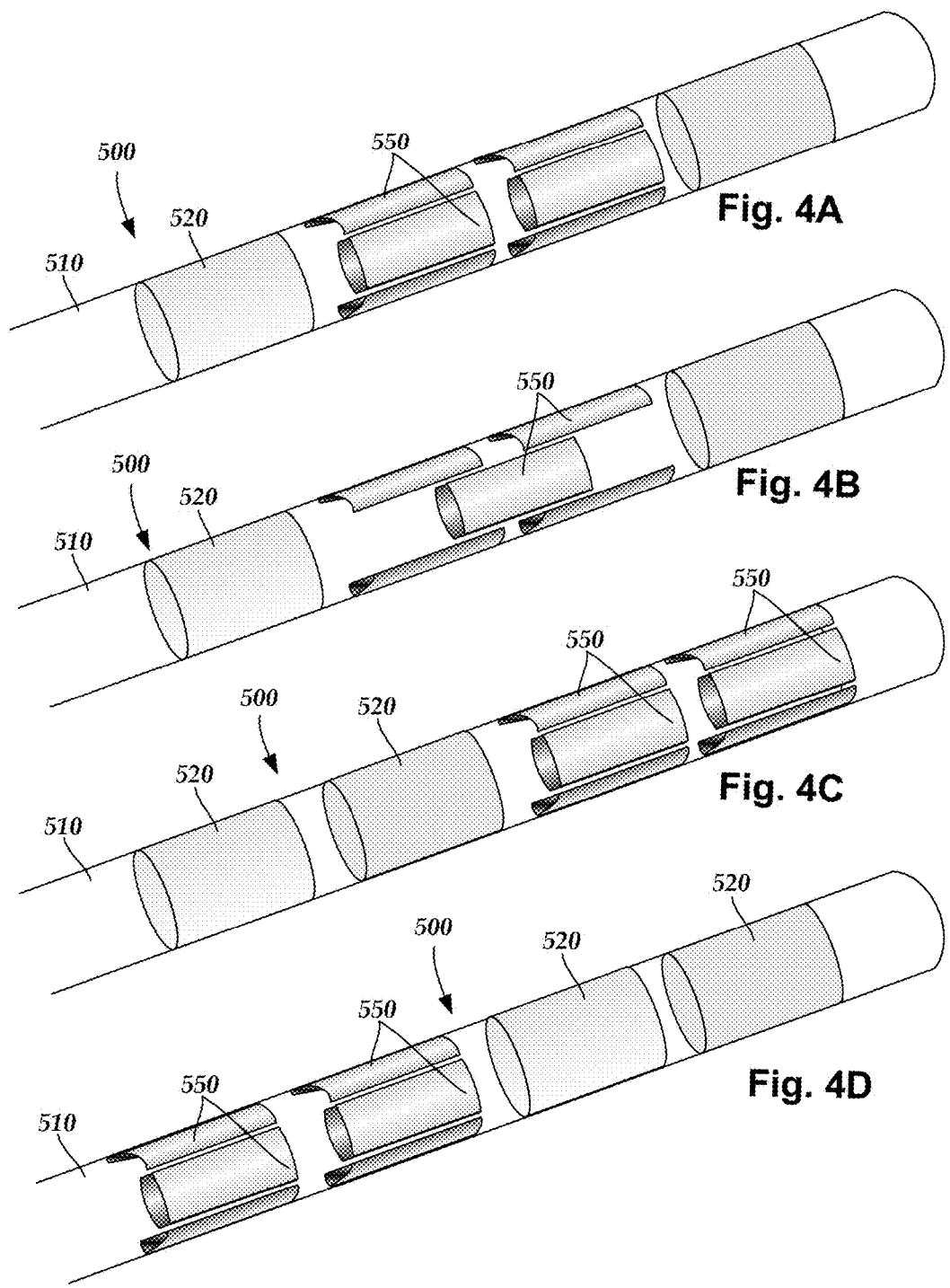

BURR HOLE PLUGS FOR ELECTRICAL STIMULATION SYSTEMS AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/196,184, filed Jul. 23, 2015, which is incorporated herein by reference.

FIELD

The present invention is directed to the area of implantable electrical stimulation systems and methods of making and using the systems. The present invention is also directed to burr hole plugs and implantable electrical stimulation systems including the burr hole plugs, as well as methods of making and using the burr hole plugs and electrical stimulation systems.

BACKGROUND

Implantable electrical stimulation systems have proven therapeutic in a variety of diseases and disorders. For example, stimulation of the brain, such as deep brain stimulation, can be used to treat a variety of diseases or disorders and spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the brain, nerves, or other tissue to be stimulated. The pulse generator in the control module generates electrical pulses that are delivered by the electrodes to body tissue.

BRIEF SUMMARY

One embodiment is a burr hole plug for use with an electrical stimulation lead including a proximal end and a plurality of terminals disposed along the proximal end. The burr hole plug includes a first plug base defining a burr hole aperture and including first grooves disposed around a circumference of the first plug base to receive at least one first portion of the electrical stimulation lead; a second plug base to be disposed around the first plug base and including second grooves disposed around a circumference of the second plug base to receive at least one second portion of the electrical stimulation lead including the terminals disposed along the proximal end of the electrical stimulation lead; a cover to be disposed on, and coupled to, the second plug base and to cover the second grooves; a cap to be disposed over the burr hole aperture and coupled to the first plug base; and an extension coupled to, and extending away from, the cover. The extension includes conductors and the second plug base and the cover include conductive elements to electrically couple the terminals of the electrical stimulation lead, when disposed in the second grooves, to the conductors of the extension.

In at least some embodiments, the grooves of the second plug base are uniformly spaced around the circumference of the second plug base. In at least some embodiments, the conductive elements include conductive contacts disposed in the second grooves of the second plug base. In at least some embodiments, the conductive elements include contacts disposed in the cover to electrically couple to the terminals of the electrical stimulation lead disposed in the second grooves of the second plug base and conductors extending along the cover from the plurality of contacts to the extension.

In at least some embodiments, the first plug base includes fastener apertures to receive a fastener to fasten the first plug base to a patient. In at least some embodiments, the second plug base includes fastener apertures to receive a fastener to fasten the first plug base to a patient. In at least some embodiments, the first and second plug bases form a single integral component.

Another embodiment is a system for electrical stimulation that includes any of the burr hole plugs described above, and an electrical stimulation lead for coupling to the burr hole plug. In at least some embodiments, the electrical stimulation lead includes a proximal end with separable branches and terminals disposed along the proximal end, each of the branches including at least one of the terminals.

A further embodiment is a method of implanting an electrical stimulation lead that includes inserting a distal end of an electrical stimulation lead into patient tissue; positioning at least one first portion of a proximal end of the electrical stimulation lead in at least one of the first grooves of the first plug base of any of the burr hole plugs described above; positioning at least one second portion of the proximal end of the electrical stimulation lead in at least one of the second grooves of the second plug base of the burr hole plug, where each of the at least one second portion includes at least one terminal of the electrical stimulation lead; attaching the cover the second plug base; and attaching the cap to the first plug base.

Yet another embodiment is a burr hole plug for use with an electrical stimulation lead including a proximal end and terminals disposed along the proximal end. The burr hole plug includes a plug base defining a burr hole aperture and including at least one groove to receive a portion of the electrical stimulation lead; a cap to be disposed over the burr hole aperture and coupled to the first plug base; a lead connector disposed on the cap and including a connector aperture to receive the proximal end of the electrical stimulation lead, the lead connector including connector contacts disposed within the connector to electrically couple to the plurality of terminals of the electrical stimulation lead when the proximal end of the electrical stimulation lead is received in the lead connector; and an extension coupled to, and extending away from, the cap. The extension includes conductors and the lead connector and the cap include conductors to electrically couple the terminals of the electrical stimulation lead, when disposed in the lead connector, to the conductors of the extension.

In at least some embodiments, the lead connector and the cap are integrally formed as a single component. In at least some embodiments, the at least one groove is a plurality of grooves. In at least some embodiments, the cap and plug base are configured and arranged so that when the cap is coupled to the plug base the connector aperture is aligned with one of the at least one groove of the plug base. In at least some embodiments, the conductors of the extension form a single layer ribbon.

Another embodiment is a system for electrical stimulation that includes any of the burr hole plugs described above, and an electrical stimulation lead for coupling to the burr hole plug. In at least some embodiments, the electrical stimulation lead includes a proximal end with separable branches and terminals disposed along the proximal end, each of the branches including at least one of the terminals. In at least some embodiments, the system further includes a control module coupleable to the extension. In at least some embodiments, the system further includes a lead extension coupleable between the extension of the burr hole plug and the control module.

A further embodiments is a method of implanting an electrical stimulation lead that includes inserting a distal end of an electrical stimulation lead into patient tissue; positioning a first portion of a proximal end of the electrical stimulation lead in at least one of the grooves of the plug base of any one of the burr hole plugs described above; inserting a second portion of the proximal end of the electrical stimulation lead into the lead connector disposed on the cap of the burr hole plug, wherein the second portion includes at least one terminal of the electrical stimulation lead; and attaching the cap to the plug base.

In at least some embodiments, attaching the cap to the plug base includes attaching the cap to the plug base with the connector aperture aligned with a one of the at least one grooves of the plug base in which the portion of the proximal end of the electrical stimulation lead is positioned.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic perspective view of one embodiment of a distal end of a lead containing segmented electrodes, according to the invention;

FIG. 4B is a schematic perspective view of a second embodiment of a distal end of a lead containing segmented electrodes, according to the invention;

FIG. 4C is a schematic perspective view of a third embodiment of a distal end of a lead containing segmented electrodes, according to the invention;

FIG. 4D is a schematic perspective view of a fourth embodiment of a distal end of a lead containing segmented electrodes, according to the invention;

DETAILED DESCRIPTION

The present invention is directed to the area of implantable electrical stimulation systems and methods of making and using the systems. The present invention is also directed to burr hole plugs and implantable electrical stimulation systems including the burr hole plugs, as well as methods of making and using the burr hole plugs and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads and paddle leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734;7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818;2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent applications Ser. Nos. 12/177,823 and 13/750,725, all of which are incorporated by reference in their entirety.

Figure 1:
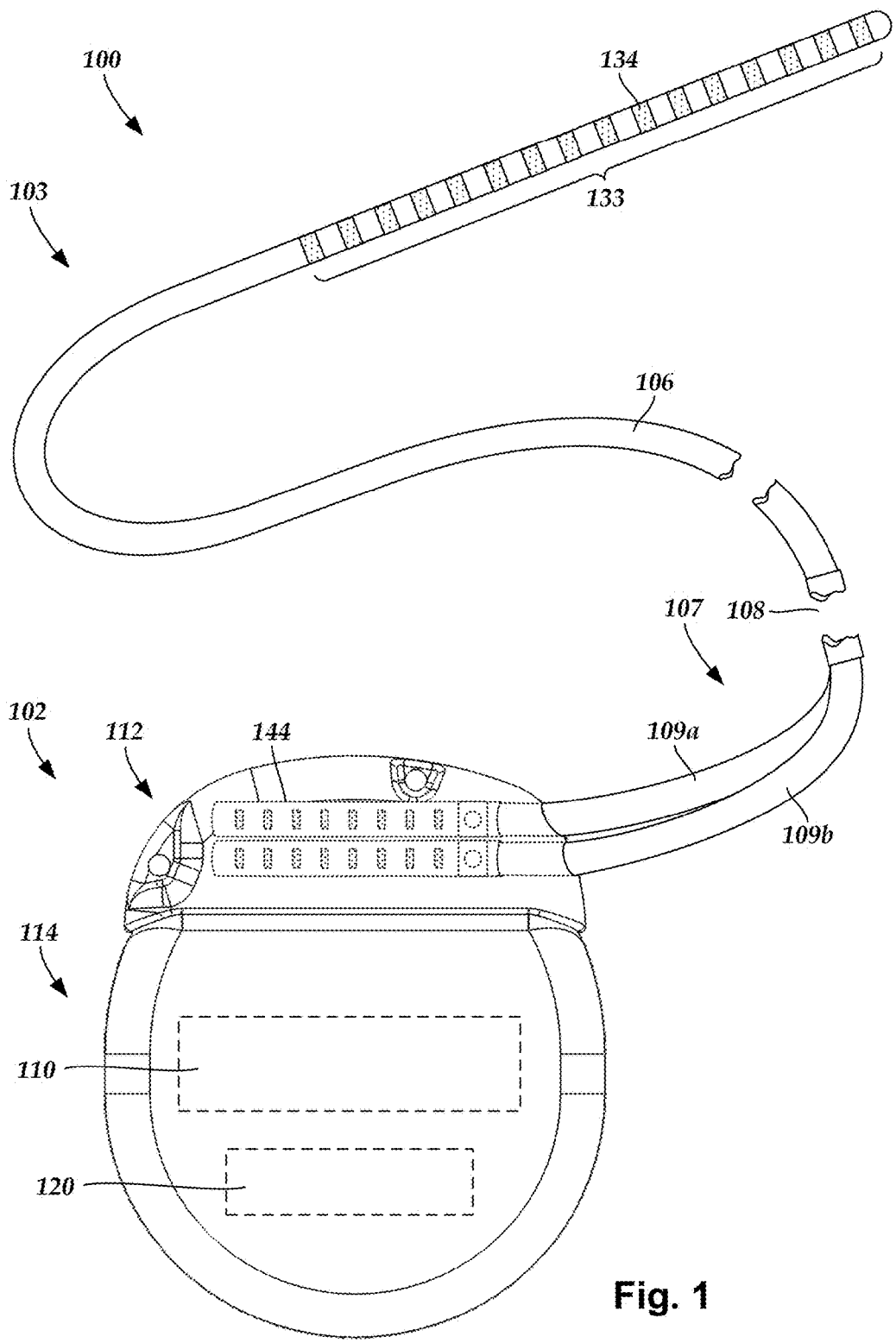
FIG. 1 is a schematic view of another embodiment of an implantable medical device that includes a percutaneous lead body coupled to a control module via a lead body, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, deep brain stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
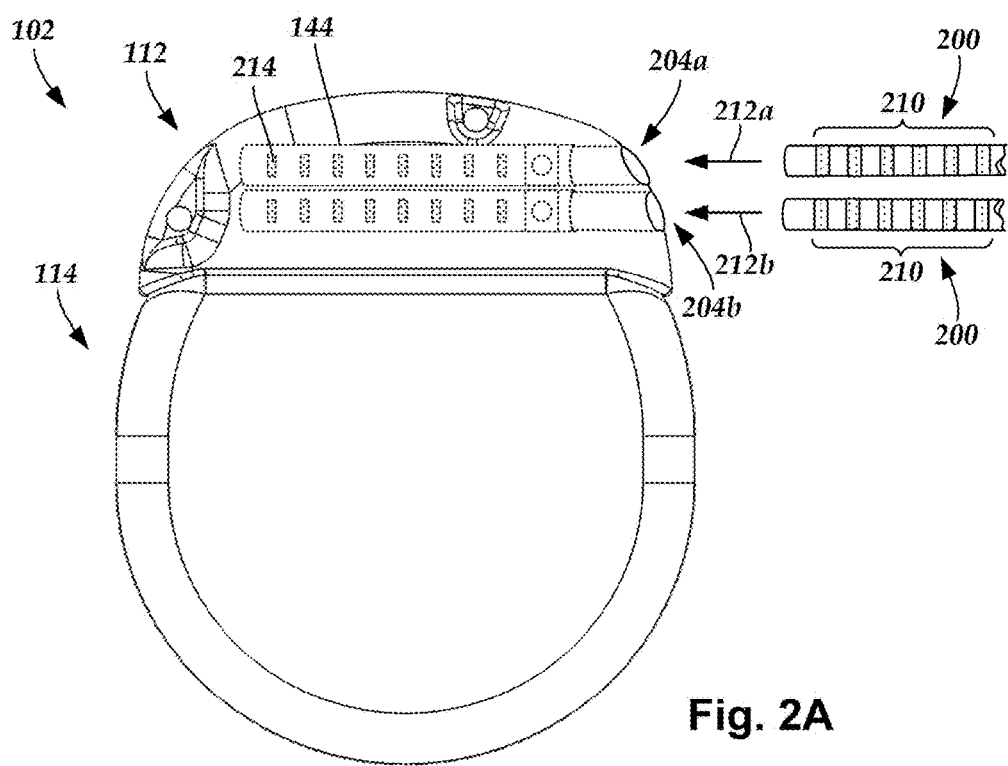
FIG. 2A is a schematic view of one embodiment of a plurality of connectors disposed in the control module of FIG. 1, the connectors configured and arranged to receive the proximal portions of the lead bodies of FIG. 1, according to the invention.
Figure 2B:
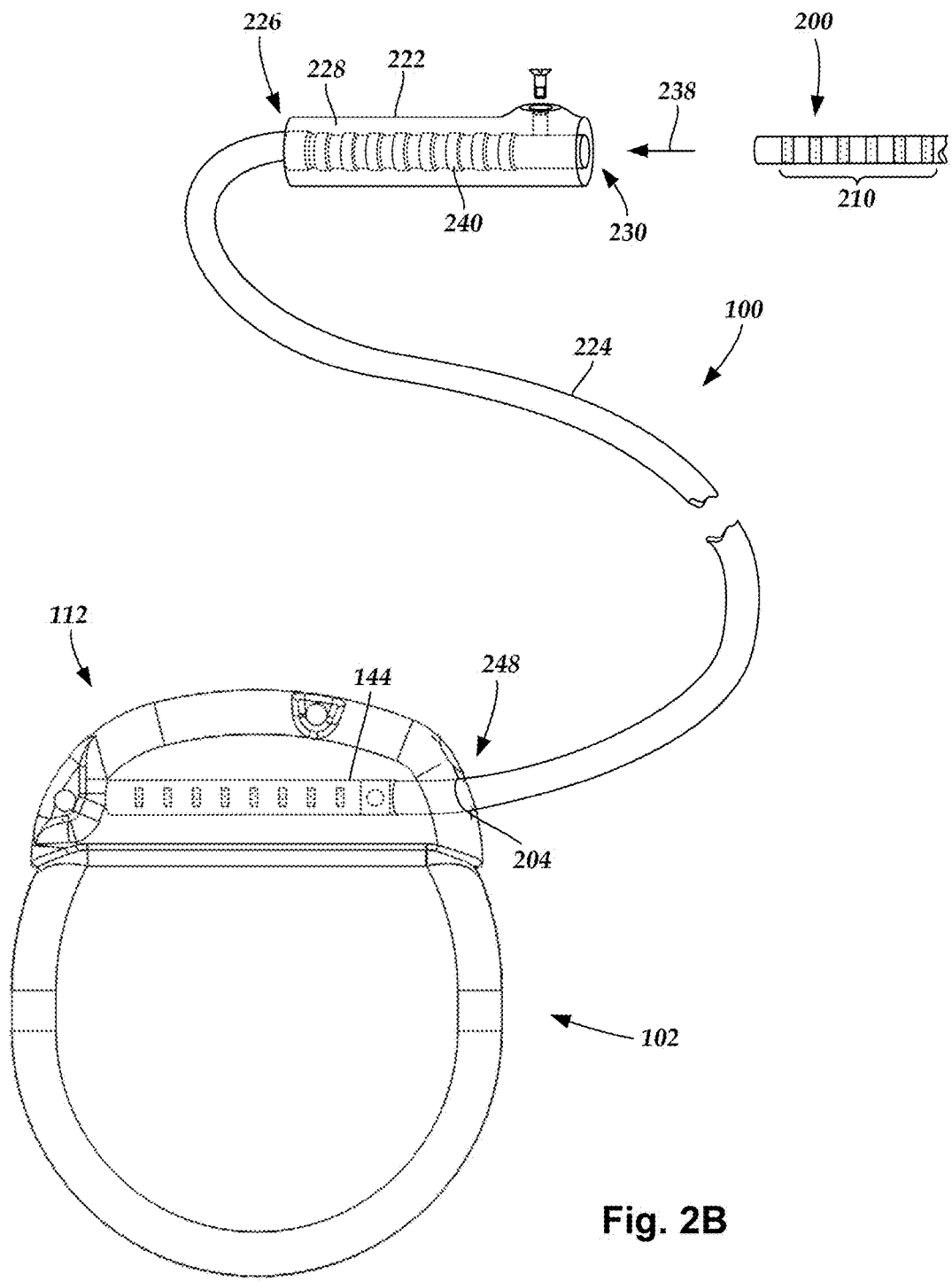
FIG. 2B is a schematic view of one embodiment of a proximal portion of the lead body of FIG. 2, a lead extension, and the control module of FIG. 2, the lead extension configured and arranged to couple the lead body to the control module, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B; and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the splitter 107 of FIG. 1, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212*b*. In FIG. 2A (and in other figures), the connector housing 112 is shown having two ports 204*a* and 204*b*. The connector housing 112 can define any suitable number of ports including, for example, one, two, three, four, five, six, seven, eight, or more ports.

The control module connector 144 also includes a plurality of connector contacts, such as connector contact 214, disposed within each port 204*a* and 204*b*. When the elongated device 200 is inserted into the ports 204*a* and 204*b*, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, all of which are incorporated by reference in their entirety.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228.

The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Figure 3:
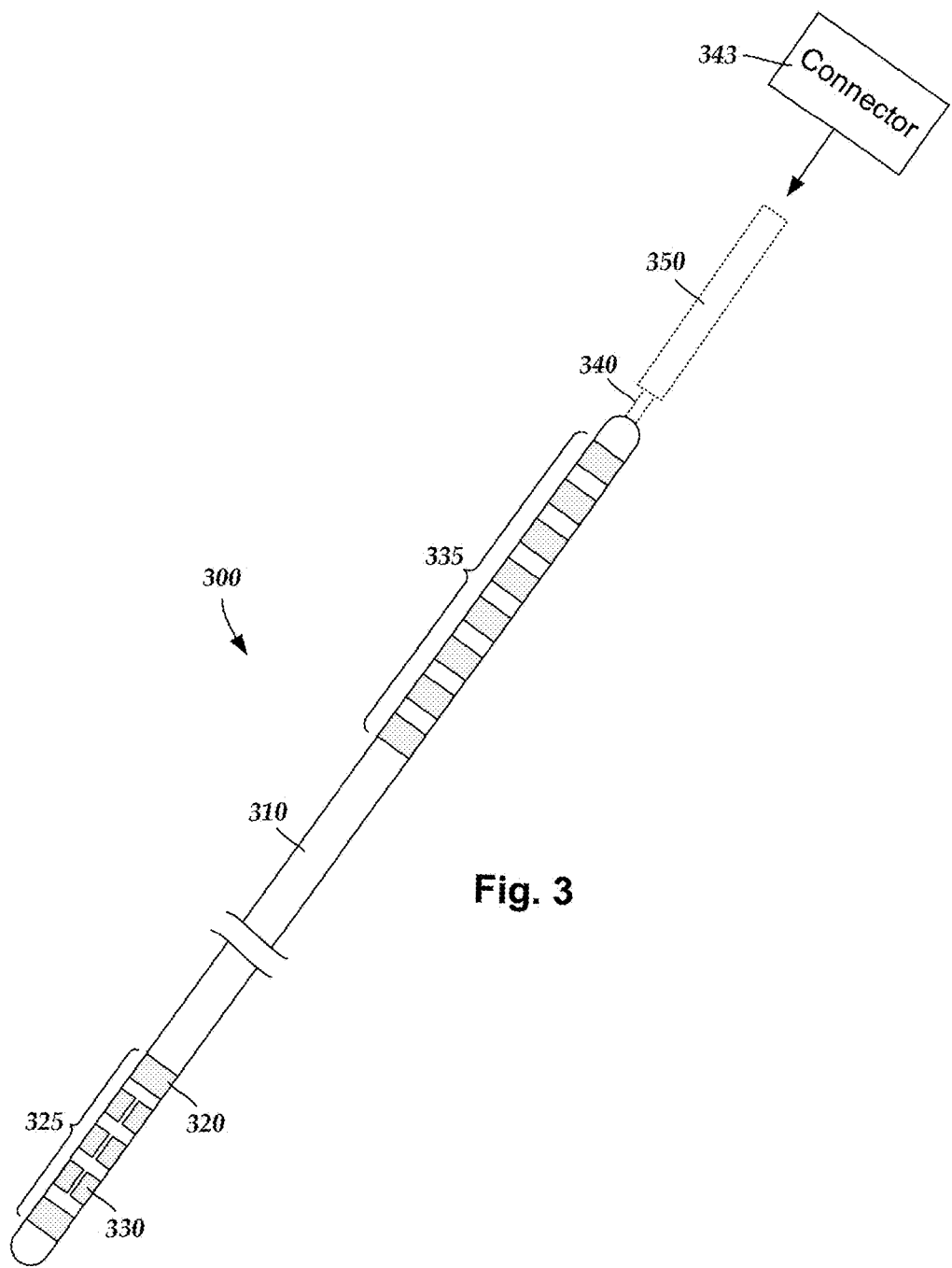
FIG. 3 is a schematic side view of yet another embodiment of an implantable medical device for brain stimulation, according to the invention.

Turning to FIG. 3, in the case of deep brain stimulation, the lead may include stimulation electrodes, recording electrodes, or a combination of both. At least some of the stimulation electrodes, recording electrodes, or both are provided in the form of segmented electrodes that extend only partially around the perimeter (for example, the circumference) of the lead. These segmented electrodes can be provided in sets of electrodes, with each set having electrodes circumferentially distributed about the lead at a particular longitudinal position.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

FIG. 3 illustrates one embodiment of a device 300 for brain stimulation. The device includes a lead 310, a plurality of electrodes 325 disposed at least partially about a perimeter of the lead 310, a plurality of terminals 335, a connector 344 for connection of the electrodes to a control unit, and a stylet 340 for assisting in insertion and positioning of the lead in the patient's brain. The stylet 340 can be made of a rigid material. Examples of suitable materials for the stylet include, but are not limited to, tungsten, stainless steel, and plastic. The stylet 340 may have a handle 350 to assist insertion into the lead 310, as well as rotation of the stylet 340 and lead 310. The connector 344 fits over a proximal end of the lead 310, preferably after removal of the stylet 340.

In FIG. 3, the electrodes 325 are shown as including both ring electrodes, such as ring electrode 320, and segmented electrodes, such as segmented electrodes 330. In some embodiments, the electrodes 325 are all segmented. In other embodiments, the electrodes 325 are all ring-shaped. In FIG. 3, each of the terminals 335 is shown as being ring-shaped. The segmented electrodes of FIG. 3 are shown in sets of two, where the two segmented electrodes of a particular set are electrically isolated from one another and are circumferentially-offset along the lead 310. Any suitable number of segmented electrodes can be formed into a set including, for example, two, three, four, or more segmented electrodes.

Segmented electrodes can be used to direct stimulus current to one side, or even a portion of one side, of the lead. When segmented electrodes are used in conjunction with an implantable pulse generator that delivers current stimulus, current steering can be achieved to more precisely deliver the stimulus to a position around an axis of the lead (i.e., radial positioning around the axis of the lead). Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a segmented electrode array, current steering can be performed not only along a length of the lead but also around a perimeter of the lead. This provides precise three-dimensional targeting and delivery of the current stimulus to neural target tissue, while potentially avoiding stimulation of other tissue. Examples of leads with segmented electrodes include U.S. Pat. Nos. 6,295,944; and 6,391,985; and U.S. Patent Applications Publication Nos. 2011/0005069; 2010/0268298; 2011/0130817; 2011/0130818; 2011/0078900; 2011/0238129; 2011/0313500; 2012/0016378; 2012/

0046710; 2012/0165911; 2012/0197375; 2012/0203316; 2012/0203320; and 2012/0203321, all of which are incorporated herein by reference in their entirety.

Figure 4E:
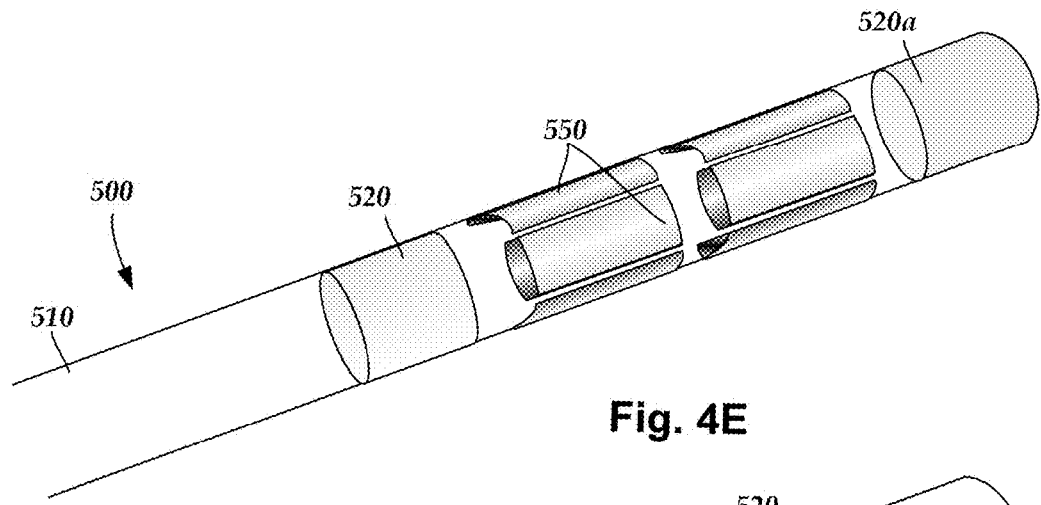
FIG. 4E is a schematic perspective view of a fifth embodiment of a distal end of a lead containing segmented electrodes, according to the invention.
Figure 4F:
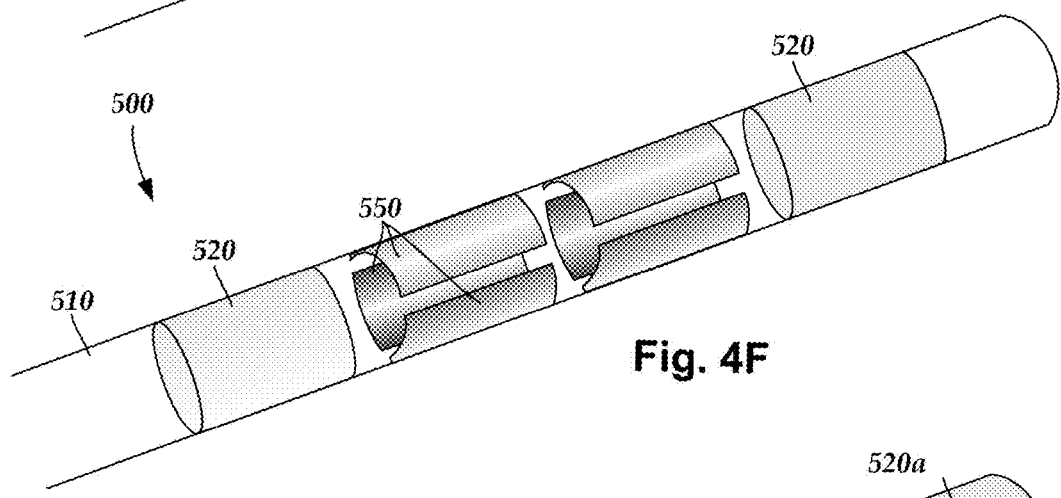
FIG. 4F is a schematic perspective view of a sixth embodiment of a distal end of a lead containing segmented electrodes, according to the invention.

FIGS. 4A-4H illustrate leads 500 with segmented electrodes 550, optional ring electrodes 520 or tip electrodes 520a, and a lead body 510. The sets of segmented electrodes 550 each include either two (FIG. 4B), three (FIGS. 4E-4H), or four (FIGS. 4A, 4C, and 4D) or any other number of segmented electrodes including, for example, three, five, six, or more. The sets of segmented electrodes 550 can be aligned with each other (FIGS. 4A-4G) or staggered (FIG. 4H).

When the lead 500 includes both ring electrodes 520 and segmented electrodes 550, the ring electrodes 520 and the segmented electrodes 550 may be arranged in any suitable configuration. For example, when the lead 500 includes two ring electrodes 520 and two sets of segmented electrodes 550, the ring electrodes 520 can flank the two sets of segmented electrodes 550 (see e.g., FIGS. 3, 4A, and 4E-4H). Alternately, the two sets of ring electrodes 520 can be disposed proximal to the two sets of segmented electrodes 550 (see e.g., FIG. 4C), or the two sets of ring electrodes 520 can be disposed distal to the two sets of segmented electrodes 550 (see e.g., FIG. 4D). One of the ring electrodes can be a tip electrode (see, tip electrode 520a of FIGS. 4E and 4G). It will be understood that other configurations are possible as well (e.g., alternating ring and segmented electrodes, or the like).

By varying the location of the segmented electrodes 550, different coverage of the target neurons may be selected. For example, the electrode arrangement of FIG. 4C may be useful if the physician anticipates that the neural target will be closer to a distal tip of the lead body 510, while the electrode arrangement of FIG. 4D may be useful if the physician anticipates that the neural target will be closer to a proximal end of the lead body 510.

Figure 4G:
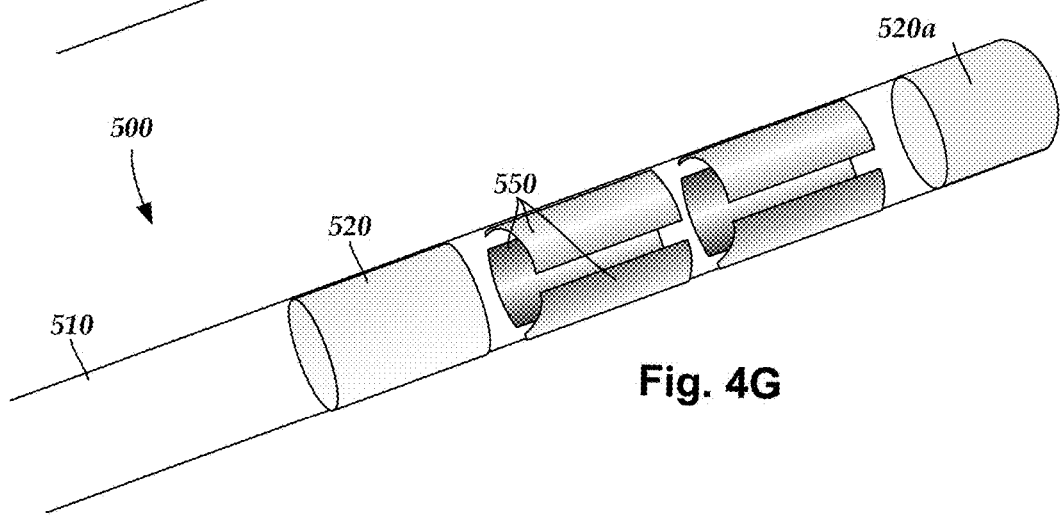
FIG. 4G is a schematic perspective view of a seventh embodiment of a distal end of a lead containing segmented electrodes, according to the invention.

Any combination of ring electrodes 520 and segmented electrodes 550 may be disposed on the lead 500. For example, the lead may include a first ring electrode 520, two sets of segmented electrodes; each set formed of four segmented electrodes 550, and a final ring electrode 520 at the end of the lead. This configuration may simply be referred to as a 1-4-4-1 configuration (FIGS. 4A and 4E—ring electrodes 520 and segmented electrode 550). It may be useful to refer to the electrodes with this shorthand notation. Thus, the embodiment of FIG. 4C may be referred to as a 1-1-4-4 configuration, while the embodiment of FIG. 4D may be referred to as a 4-4-1-1 configuration. The embodiments of FIGS. 4F, 4G, and 4H can be referred to as a 1-3-3-1 configuration. Other electrode configurations include, for example, a 2-2-1-2 configuration, where four sets of segmented electrodes are disposed on the lead, and a 4-4 configuration, where two sets of segmented electrodes, each having four segmented electrodes 550 are disposed on the lead. The 1-3-3-1 electrode configuration of FIGS. 4F, 4G, and 4H has two sets of segmented electrodes, each set containing three electrodes disposed around the perimeter of the lead, flanked by two ring electrodes (FIGS. 4F and 4H) or a ring electrode and a tip electrode (FIG. 4G). In some embodiments, the lead includes 16 electrodes. Possible configurations for a 16-electrode lead include, but are not limited to 4-4-4-4; 6-8; 5-3-3-3-3-1 (and all rearrangements of this configuration); and 2-2-2-2-2-2-2-2. Any other suitable segmented electrode arrangements (with or without ring electrodes) can be used including, but not limited to, those disclosed in U.S. Provisional Patent Application Ser. No. 62/113,291 and U.S. Patent Applications Publication Nos. 2012/0197375 and 2015/0045864, all of which are incorporated herein by reference in their entirety.

In at least some embodiments it may be advantageous to design an elongate member (e.g., a lead, lead extension, splitter, adaptor, or the like) with segmented terminals. In at least some embodiments, the elongate member also includes segmented electrodes. Utilizing segmented terminals may reduce the physical size of the terminal array when compared to conventional terminal arrays with ring-shaped terminals. Some examples of such arrangements are found in, for example, U.S. Provisional Patent Applications Ser. Nos. 62/113,291 and 62/146,017, all of which are incorporated herein by reference in their entirety.

Figure 5:
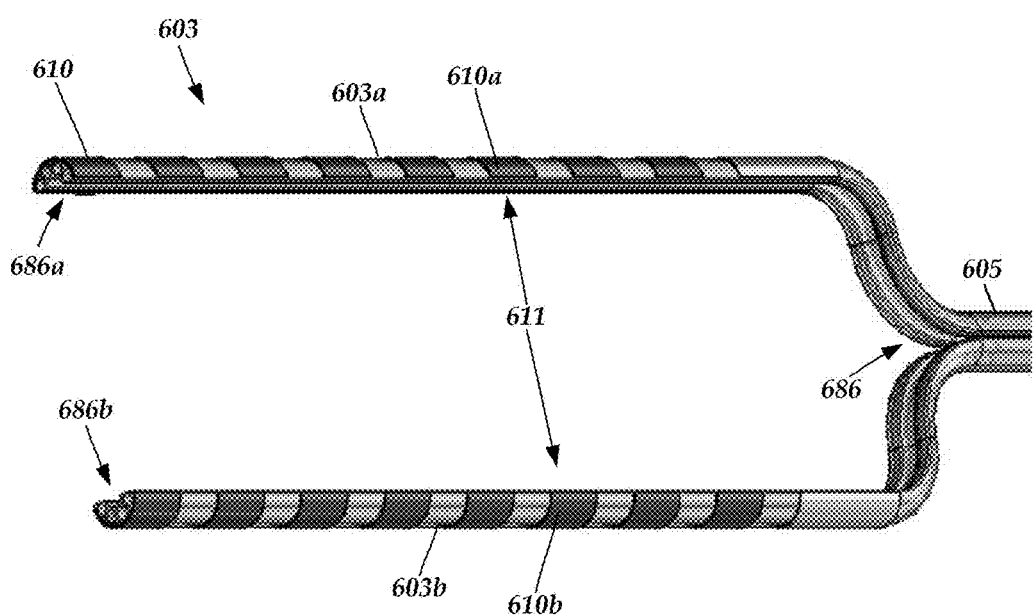
FIG. 5 is a schematic perspective side view of one embodiment of a proximal end of a lead containing segmented terminals and branches, according to the invention.

FIG. 5 illustrates one embodiment of a proximal portion of a lead 603 (or other elongate member) with an array of segmented terminals 610. The proximal end portion of the lead 603 is divided into two branches 603a, 603b with terminals 610a, 610b disposed on each branch. Although the embodiment of FIG. 5 illustrates two branches, other embodiments can have three, four, five, six, or more branches with each branch including terminals disposed on the branch. The two branches 603a, 603b join together to form a joined portion 605 of the lead 603. The lead 603 can also optionally include a central lumen 686 with separate channels 686a, 686b form in the respective branches 603a, 603b. In at least some embodiments, the two branches 603a, 603b have an arc-shaped lateral cross-sectional shape.

The segmented terminals 610 can be formed in sets 611 of two or more terminals at a same position along the longitudinal axis of the lead. Each of the segmented terminals of a particular set extends around less than (for example, no more than 45%, 40%, 33%, 30%, or 25% of) the entire perimeter of the elongate member. The segmented terminals of the set are not in electrical contact with one another and are circumferentially-offset from one another along the elongate member. In at least some embodiments, the terminal array includes at least one segmented terminal set, such as segmented terminal set 611 which, in turn, includes multiple segmented terminals 610, such as segmented terminals 610a and 610b. In some embodiments, a set of segmented terminals can have two, three, four, or more segmented terminals disposed at the same position along the longitudinal axis of the elongate member, but circumferentially offset from each other.

The terminal array can include any suitable number of segmented terminal sets 611 including, for example, one, two, three, four, five, six, seven, eight, nine, ten eleven, twelve, thirteen, fourteen, fifteen, sixteen, or more segmented-terminal sets. In FIG. 5, eight segmented terminal sets 611 are shown disposed along the lead 603.

In at least some embodiments, the terminal 610 of each set are aligned with each other to form longitudinal columns (i.e., columns parallel to the longitudinal axis of the lead) of terminals that are aligned. In other embodiments, the segmented terminals 610 can be arranged in longitudinal columns that are longitudinally offset from each other with the terminals of different longitudinal columns that do or do not overlap. It will be recognized that other arrangements of segmented terminals, including any of those arrangements described above with respect to arrangements of segmented terminals, can be used.

Figure 6A:
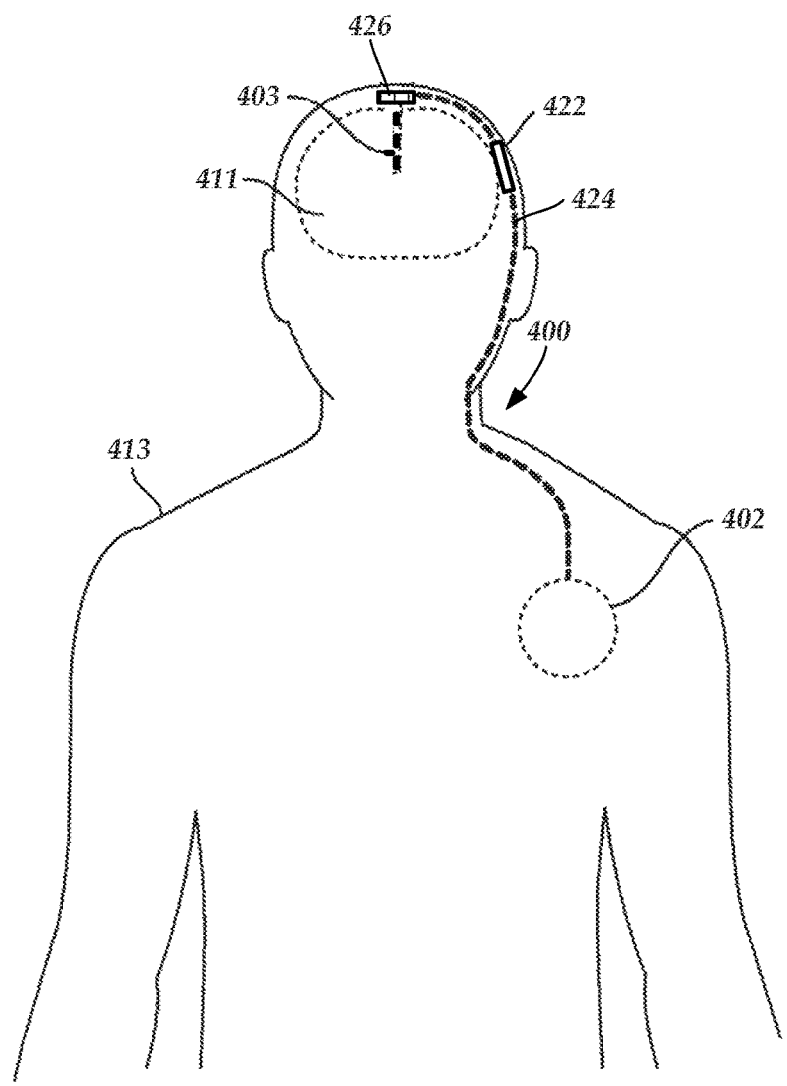
FIG. 6A is a schematic view of one embodiment of an electrical stimulation system with a lead implanted in a brain of patient, according to the invention.

FIG. 6A illustrates one example of an electrical stimulation system 400 for deep brain stimulation of the brain 411 of a patient 413. The electrical stimulation system includes a lead 403, a control module 402, and an optional extension 424 which includes a connector 422 that receives the proximal end of the lead. It will be understood that the lead and other system components can be implanted elsewhere to achieve other types of stimulation including, but not limited to, spinal cord stimulation or stimulation of other body organs.

Figure 6B:
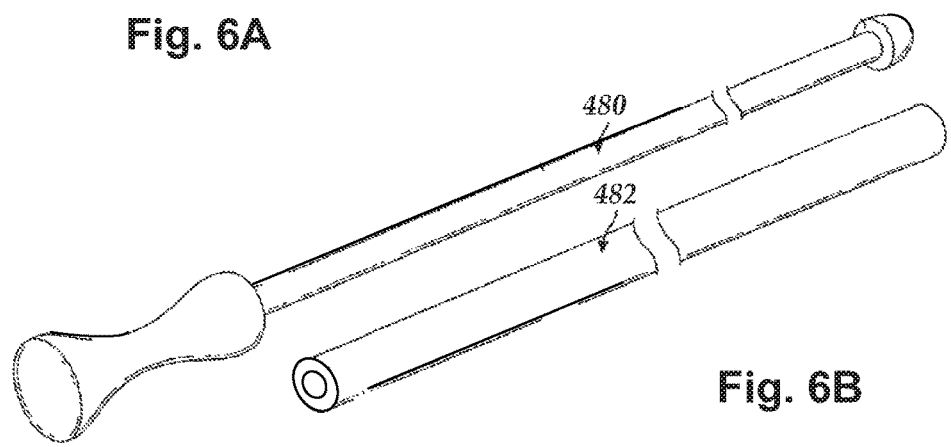
FIG. 6B is a schematic perspective view of one embodiment of tools useful for implanting the electrical stimulation system, according to the invention.

The distal end of the lead 403 is implanted at the stimulation site and the lead extends through a burr hole in the skull of the patient. A burr hole plug 426 is placed on the skull around the burr hole and the lead 403 passes through the burr hole plug. The control module 402 is typically implanted elsewhere in the body, such as in the torso of the patient or in a subcutaneous pocket. In at least some embodiments, a tunnel (for example, a subcutaneous tunnel) can be formed between the implantation sites of the lead and control module using a tunneling tool 480, as illustrated in FIG. 6B, over which a tunneling sheath 482 is disposed. After forming the tunnel, the tunneling tool 480 can be removed leaving the tunneling sheath 482 and a portion of the lead or a lead extension is slidingly inserted into and through the tunneling sheath.

Figure 7A:
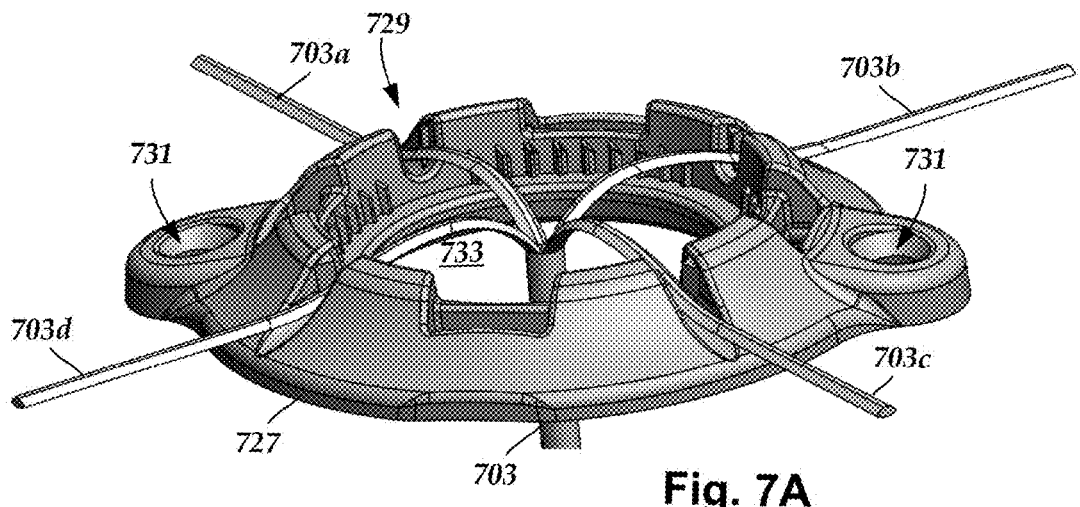
FIG. 7A is a schematic perspective view of a first plug base of one embodiment of a burr hole plug and a proximal portion of one embodiment of an electrical stimulation lead, according to the invention.
Figure 7B:
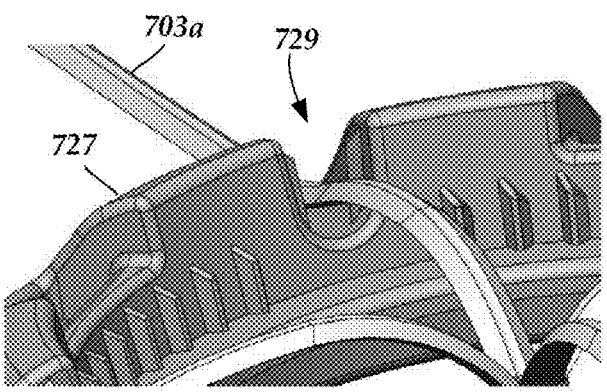
FIG. 7B is a schematic perspective close-up view of a portion of the first plug base and electrical stimulation lead of FIG. 7A, according to the invention.
Figure 7C:
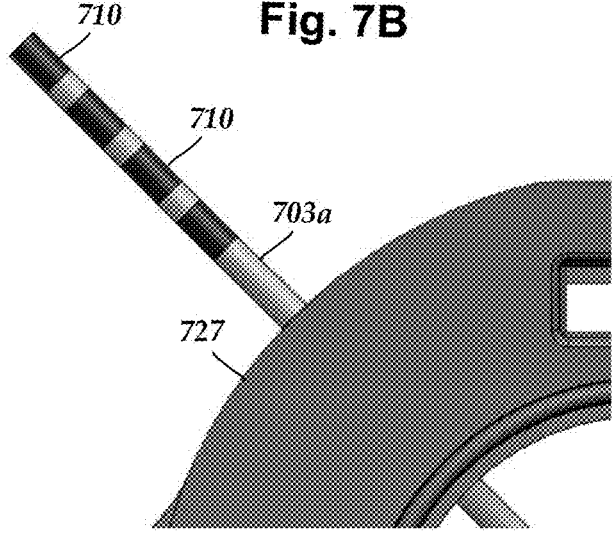
FIG. 7C is a schematic close-up bottom view of a portion of the first plug base and electrical stimulation lead of FIG. 7A, according to the invention.

FIG. 7A-7H illustrate one embodiment of a burr hole plug 726 (FIGS. 7F-7H) to be used with a lead having segmented terminals that can be divided into two or more branches, as illustrated in FIG. 5. FIGS. 7A-7C illustrate a first plug base 727 and a lead 703 which, in the illustrated embodiment, can be divided into four branches 703a, 703b, 703c, 703d with each branch carrying segmented terminals 710 (FIG. 7C). In other embodiments, the lead can have two, three, five, six, or more branches. The first plug base 727 can be made of any suitable material including, but not limited to, rigid plastics, metals, or alloys. In at least some embodiments, if the first plug base 727 is made of metal or alloy the first plug base may also include a non-conductive polymer disposed over all or part of the metal or alloy.

The first plug base 727 defines grooves 729 through which each branch 703a, 703b, 703c, 703d passes. The first plug base 727 preferably includes at least one groove 729 for each branch, but may include more grooves than the lead has branches. The branches 703a, 703b, 703c, 703d extend beyond the first plug base 727 with the segmented terminals 710 disposed outside the first plug base, as illustrated in FIG. 7C.

The first plug base 727 also defines one or more fastener apertures 731 through the first plug base. A fastener (not shown), such as a screw or rod, can be inserted into the fastener aperture 731 of the first plug base and used to secure the first plug base to the skull of the patient. The first plug base 727 also defines a burr hole aperture 733 that is placed over the burr hole and through which the lead 703 extends into the first plug base.

Figure 7D:
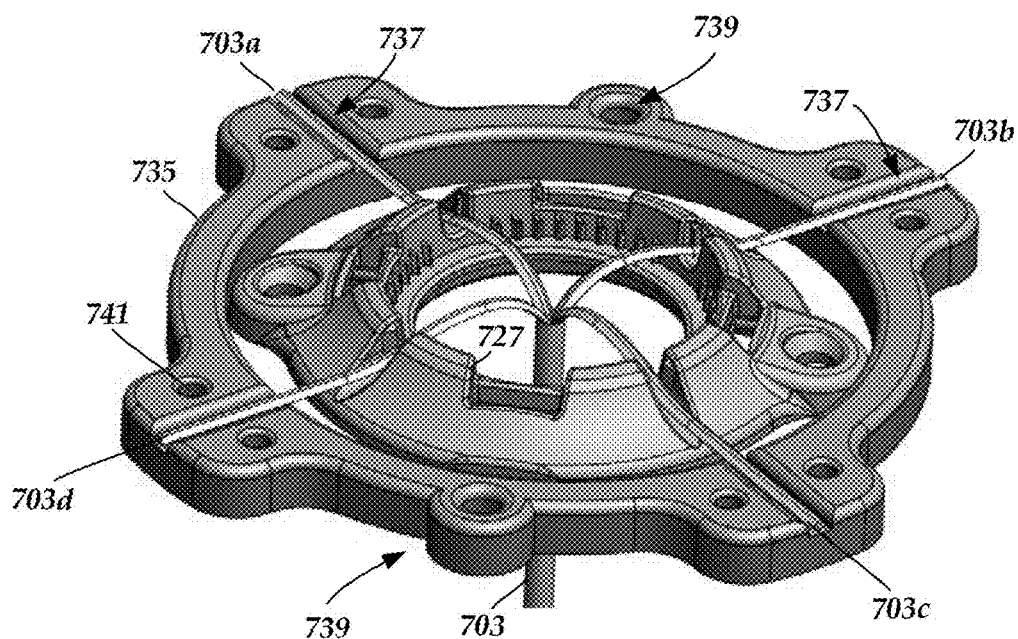
FIG. 7D is a schematic perspective view of a second plug base of one embodiment of a burr hole plug and the first plug base of FIG. 7A, according to the invention.
Figure 7E:
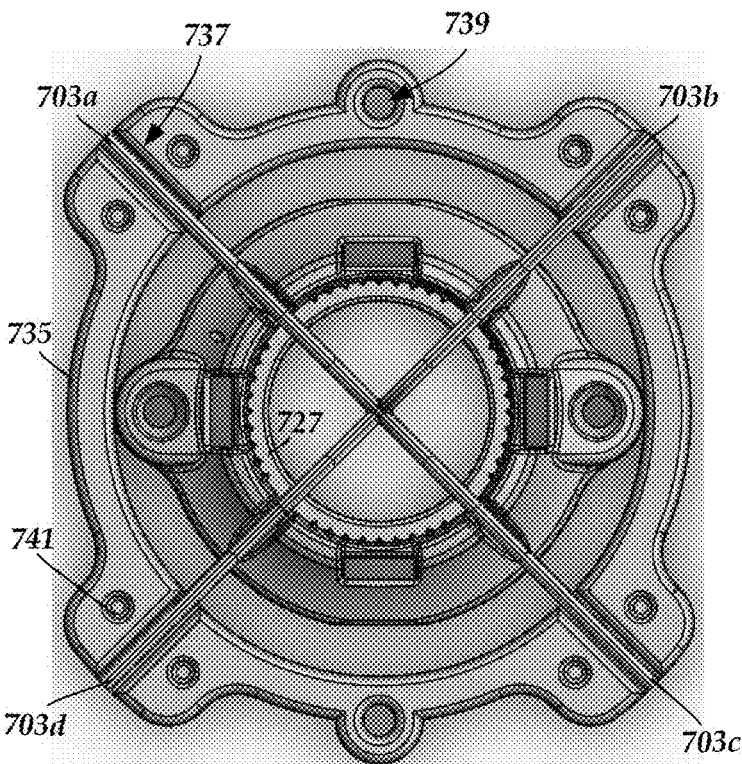
FIG. 7E is a schematic top view of the first and second plug bases of FIG. 7D, according to the invention.

FIGS. 7D and 7E illustrate a second plug base 735 that fits outside and around the first plug base 727. In some embodiments, the first plug base 727 and the second plug 735 are separate components. In other embodiments, the first and second plug bases 727, 735 can form a single, integrated component.

The second plug base 735 includes grooves 737 to receive the ends of the branches 703a, 703b, 703c, 703d of the lead 703 and, in particular, to receive the segmented terminals 710 (FIG. 7C) disposed on those branches. The body of the second plug base 735 is made of a non-conductive material and the second plug base includes conductive contacts (not shown) disposed within the grooves 737 to make electrical contact with the segmented terminals 710 of the branches 703a, 703b, 703c, 703d of the lead 703. Preferably, the contacts in each groove 737 are spaced apart with the same spacing as the segmented terminals 710 of the corresponding branch 703a, 703b, 703c, 703d. The contacts can be attached, molded, or otherwise coupled to the second plug base 735

The second plug base 735 defines one or more fastener apertures 739 through the second plug base. A fastener (not shown), such as a screw or rod, can be inserted into the fastener aperture 739 of the second plug base and used to secure the second plug base to the skull of the patient. The second plug base 735 can also define one or more apertures 741 for receiving pins (not shown) or the like from the cover 743 (FIG. 7F) to fasten the cover 743 to the second plug base 735. In an alternative arrangement, the second plug base can have pins extending from the second plug base to fit into apertures in the cover. Any other suitable method for reliably coupling the cover 743 to the second plug base 735 can be use.

Figure 7F:
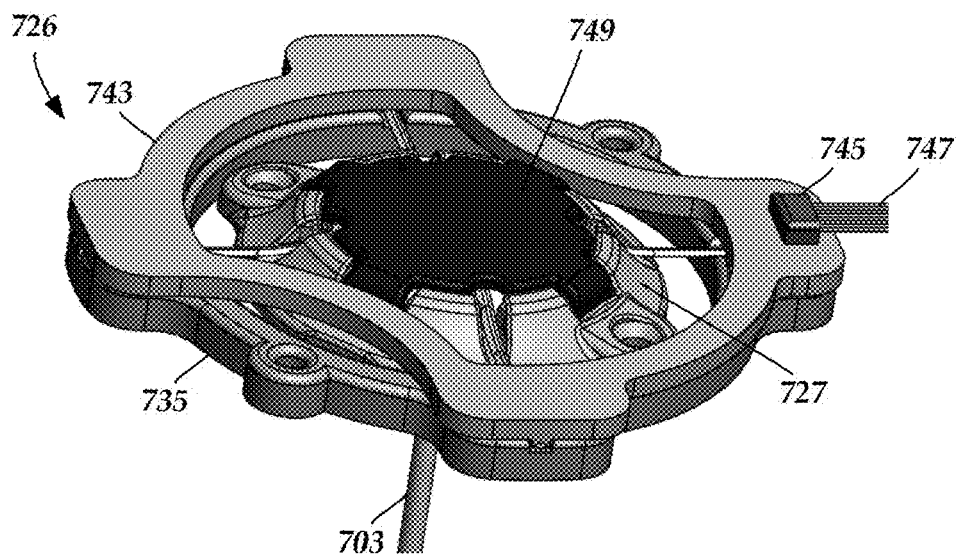
FIG. 7F is a schematic perspective view of one embodiment of a burr hole plug and a proximal portion of one embodiment of an electrical stimulation lead including the first and second plug bases of FIGS. 7A-7E, according to the invention.
Figure 7G:
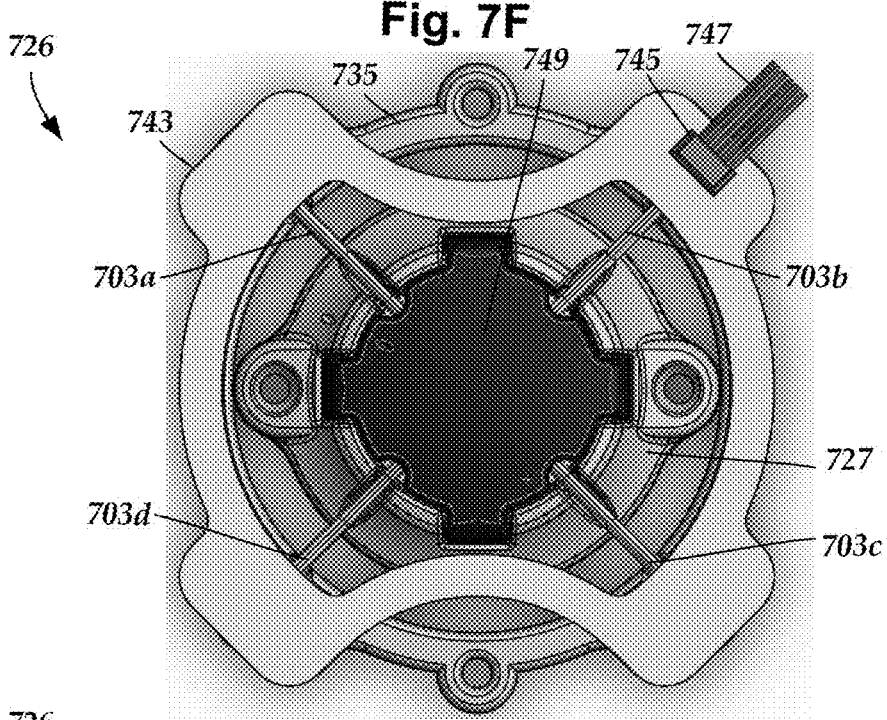
FIG. 7G is a schematic top view of the burr hole plug of FIG. 7F, according to the invention.
Figure 7H:
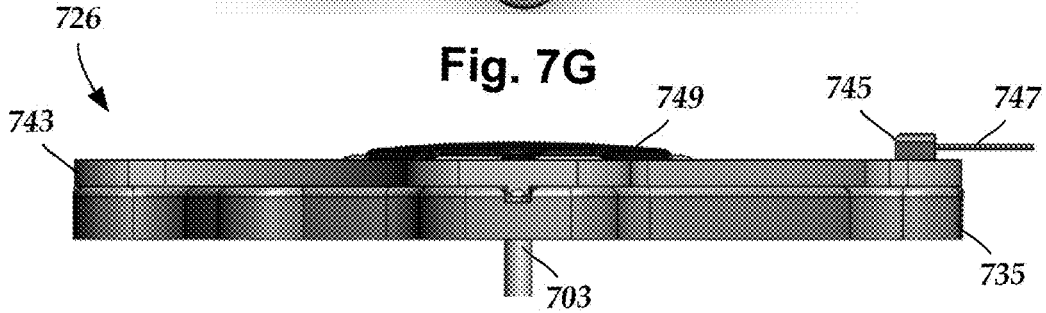
FIG. 7H is a schematic side view of the burr hole plug of FIG. 7F, according to the invention.
Figure 8A:
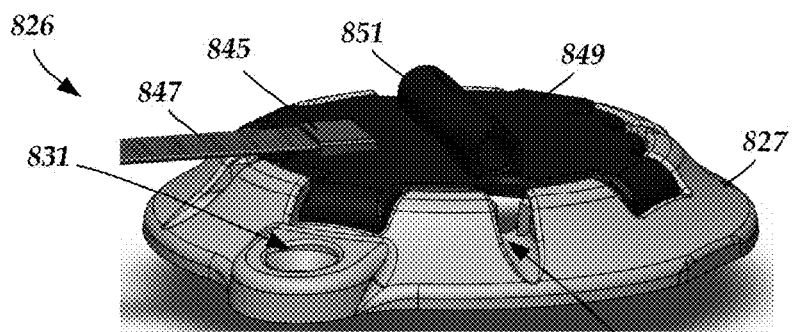
FIG. 8A is a schematic perspective view of another embodiment of a burr hole plug, according to the invention.
Figure 8B:
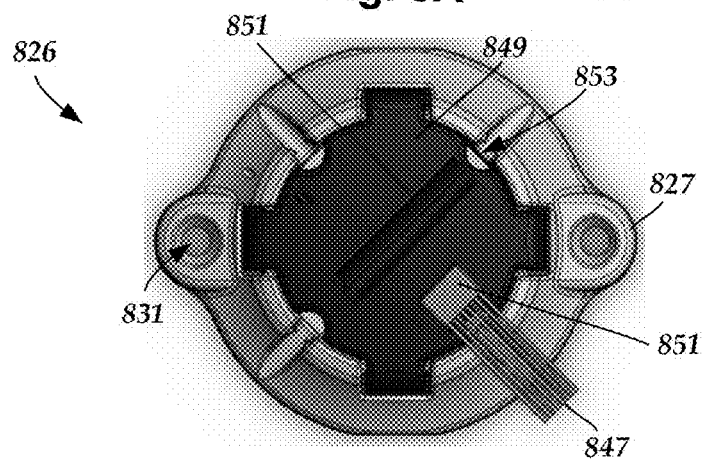
FIG. 8B is a schematic top view of the burr hole plug of FIG. 8A, according to the invention.
Figure 8C:
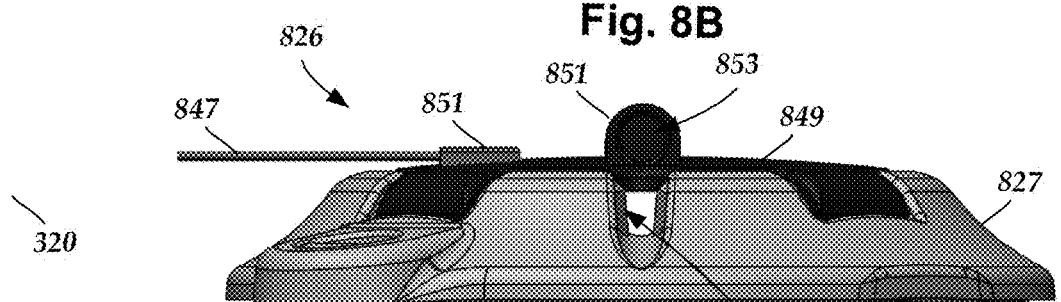
FIG. 8C is a schematic side view of the burr hole plug of FIG. 8A, according to the invention.
Figure 8D:
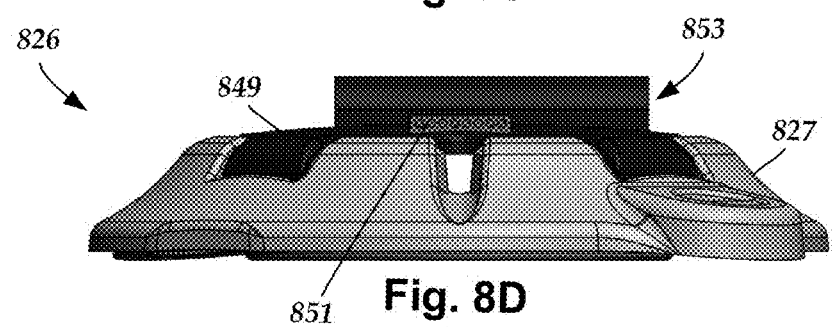
FIG. 8D is another schematic side view of the burr hole plug of FIG. 8A, according to the invention.

FIGS. 7F-7H illustrate a cover 743 that fits over at least a portion of the second plug base 735 and, in particular, over the grooves 737 in the second plug base with the ends of the lead branches 703a, 703b, 703c, 703d to hold the branches within the burr hole plug. The cover 743 also includes a connector 745 with an extension 747 extending away from the burr hole plug 726.

The cover 743 includes a base formed of a non-conductive material and also includes contacts (not shown) that make electrical contact with the conductive contacts of the second plug base 737 or the segmented terminals 710 (of both). The cover 743 further includes wires or traces (not shown) that connect the contacts of the cover to the connector 745. In some embodiments, the cover 743 can be, or can include, a flex circuit substrate with the contacts and traces/wires disposed on the flex circuit substrate. In other embodiments, the contacts or traces/wires (or both) can be molded into the cover 743 or otherwise attached to the cover.

The extension 747 includes one or more conductors (such as wires or traces) that extend away from the burr hole plug 726 and are electrically coupled to the connector 745 and the wires or traces of the cover 743. In some embodiments, the extension 747 can have the form of a ribbon with adjacent conductors. In other embodiments, the extension 747 may have a form similar to that of the leads or lead extensions disclosed above. In addition the proximal end (not shown) of the extension 747 can have terminals similar to those of the leads or lead extensions described above so that the proximal end of the extension 747 can be inserted into a connector of a lead extension or control module. In some embodiments, the extension 747 may provide a lower profile than the lead or a connector of a lead extension.

In at least some embodiments, the electrodes (not shown) of the lead 703 are electrically coupled to the wires/traces of the extension 747 through the conductors in the lead, the segmented terminals 710 of the lead, the conductive contacts in the second plug base 735, the contacts in the cover 743, the wires/traces of the cover, and the connector 745. In other embodiments, the second plug base 735 does not include conductive contacts and, instead, the segmented terminals 710 of the lead are positioned to make direct electrical contact with the contacts in the cover 743.

FIG. 7F-7H also illustrate a cap 749 that fits over the burr hole aperture 733 of the first plug base 727. The cap 749 can be made out of any suitable material include polymers, metals, and alloys. The cap 749 preferably fits tightly on the first plug base 727 using, for example, a friction fit, a compression fit, or one or more interlocking features. Examples of arrangements for holding a cap on a plug base can be found in U.S. Patent Application Publications Nos. 2009/0011237; 2010/10145357; 2013/0006410; and 2013/

0066430, all of which are incorporated herein by reference in their entirety. In some embodiments, the cover 743 and the cap 749 are separate components. In other embodiments, the cover 743 and the cap 749 can form a single, integrated component.

FIGS. 8A-8D illustrate another embodiment of a burr hole plug 826 that includes a plug base 827, a cap 849, a connector 845, an extension 847, and a lead connector 851. The plug base 827 can be similar to the first plug base 727 and includes at least one groove 829 from which a lead (not shown) can exit. A lead suitable for this embodiment may or may not have segmented terminals and may or may not have branches.

The plug base 827 also defines one or more fastener apertures 831 through the plug base. A fastener (not shown), such as a screw or rod, can be inserted into the fastener aperture 831 of the plug base and used to secure the plug base to the skull of the patient. The plug base 827 also defines a burr hole aperture (not shown) that is placed over the burr hole and through which the lead extends into the plug base. The plug base 827 can be made of any suitable material including, but not limited to, rigid plastics, metals, or alloys. In at least some embodiments, if the plug base 827 is made of metal or alloy the first plug base may also include a non-conductive polymer disposed over all or part of the metal or alloy.

The cap 849 fits over the burr hole aperture of the plug base 827. The cap 849 can be made out of any suitable material include polymers, metals, and alloys. The cap 849 preferably fits tightly on the plug base 827 using, for example, a friction fit, a compression fit, or one or more interlocking features, Examples of arrangements for holding a cap on a plug base can be found in U.S. Patent Application Publications Nos. 2009/0011237; 2010/0145357; 2013/0006410; and 2013/0066430, all of which are incorporated herein by reference in their entirety. In some embodiments, the cap 849 may also include features that fill all other grooves, if any, of the plug base other than the one from which lead extends.

The lead connector 851 is disposed on top of the cap 849 and has at least one aperture 853 into which a proximal portion of the lead can be inserted. In other embodiments, the burr hole plug can include multiple lead connectors 851 disposed on the cap to allow multiple leads or branches of a lead to be individually inserted into different lead connectors. In at least some embodiments, the cap 849 and lead connector 851 are arranged so that the cap can be fit on the plug base 827 with the aperture 853 of the lead connector aligned with one of the grooves 829 of the plug base. The lead connector 851 and the cap 849 can for a single integral unit which may be molded or otherwise formed together. Alternatively, the lead connector 851 can be attached to the cap 849 by adhesive, fasteners, or using any other attachment method or element.

The lead connector 851 includes conductive contacts within a conductor lumen that extends from the aperture 853. For example, the lead connector 851 can be the same or similar to the connector 222 illustrated in FIG. 2B. Other examples of connectors that can be used or modified for use as the lead connector 851 can be found in the references cited above. In addition, U.S. Provisional Patent Applications Ser. Nos. 62/113,291 and 62/146,017, both of which are incorporated herein by reference in their entirety, disclose connectors that can be used with leads having segmented terminals and which can be used for the lead connector 85.

The cap 849 includes wires or traces (not shown) that connect the contacts of the lead connector 851 to the connector 845. In some embodiments, the cap 849 can include a flex circuit substrate with the contacts and traces/wires disposed on the flex circuit substrate. In other embodiments, the traces/wires can be molded into the cap 849 or otherwise attached to the cover.

The extension 847 includes one or more conductors (such as wires or traces) that extend away from the burr hole plug 826 and are electrically coupled to the connector 845 and the wires or traces of the cap 843. In some embodiments, the extension 847 can have the form of a ribbon with adjacent conductors. In other embodiments, the extension 847 may have a form similar to that of the leads or lead extensions disclosed above. In addition the proximal end (not shown) of the extension 847 can have terminals similar to those of the leads or lead extensions described above so that the proximal end of the extension 847 can be inserted into a connector of a lead extension or control module.

In at least some embodiments, the electrodes (not shown) of the lead 703 are electrically coupled to the wires/traces of the extension 847 through the conductors in the lead, the segmented terminals of the lead, the conductive contacts in the lead connector 851, the wires/traces of the cap 849, and the connector 845.

Figure 9:
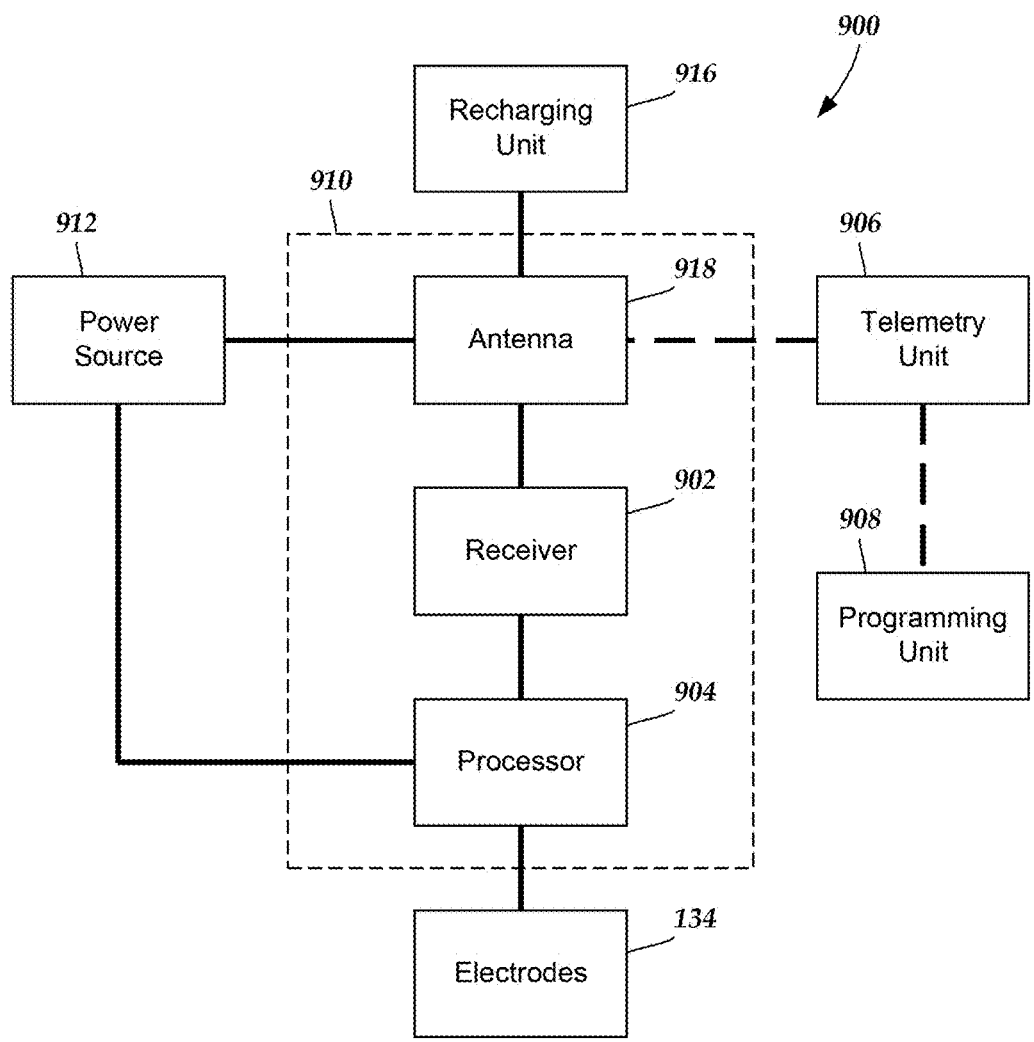
FIG. 9 is a schematic overview of one embodiment of components of an electrical stimulation system, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, power source 912, antenna 918, receiver 902, and processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference in its entirety.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 may select which electrode(s) are cathodes and which electrode(s) are anodes. In some embodiments, the processor 904 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by a programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include an antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A burr hole plug for use with an electrical stimulation lead comprising a proximal end and a plurality of terminals disposed along the proximal end, the burr hole plug comprising:
   a first plug base defining a burr hole aperture and comprising a plurality of first grooves disposed around a circumference of the first plug base and configured and arranged to receive at least one first portion of the electrical stimulation lead;
   a second plug base configured and arranged to be disposed around the first plug base and comprising a plurality of second grooves disposed around a circumference of the second plug base and configured and arranged to receive at least one second portion of the electrical stimulation lead including the plurality of terminals disposed along the proximal end of the electrical stimulation lead;
   a cover configured and arranged to be disposed on, and coupled to, the second plug base and to cover the plurality of second grooves;
   a cap configured and arranged to be disposed over the burr hole aperture and coupled to the first plug base; and
   an extension coupled to, and extending away from, the cover, the extension comprising a plurality of conductors, wherein the second plug base and the cover comprise a plurality of conductive elements configured and arranged to electrically couple the plurality of terminals of the electrical stimulation lead, when disposed in the second grooves, to the plurality of conductors of the extension.

2. The burr hole plug of claim 1, wherein the plurality of second grooves of the second plug base are uniformly spaced around the circumference of the second plug base.

3. The burr hole plug of claim 1, wherein the conductive elements comprise a plurality of conductive contacts disposed in the second grooves of the second plug base.

4. The burr hole plug of claim 1, wherein the conductive elements comprise a plurality of contacts disposed in the cover and configured and arranged to electrically couple to the terminals of the electrical stimulation lead disposed in the second grooves of the second plug base and a plurality of conductors extending along the cover from the plurality of contacts to the extension.

5. The burr hole plug of claim 1, wherein the first plug base comprises a plurality of fastener apertures configured and arranged to receive a fastener to fasten the first plug base to a patient.

6. The burr hole plug of claim 1, wherein the second plug base comprises a plurality of fastener apertures configured and arranged to receive a fastener to fasten the second plug base to a patient.

7. The burr hole plug of claim 1, wherein the first and second plug bases form a single integral component.

8. The burr hole plug of claim 1, wherein the conductors of the extension form a single layer ribbon.

9. The burr hole plug of claim 1, wherein the second plug base comprises a body made of a non-conductive material.

10. The burr hole plug of claim 9, wherein the conductive elements are disposed in the body of the second plug base.

11. The burr hole plug of claim 1, wherein the cap forms a friction fit or compression fit with the first plug base.

12. A system for electrical stimulation, comprising:
    an electrical stimulation lead comprising a proximal end and a plurality of terminals disposed along the proximal end; and a burr hole plug for use with the electrical stimulation lead, the burr hole plug comprising:
- a first plug base defining a burr hole aperture and comprising a plurality of first grooves disposed around a circumference of the first plug base and configured and arranged to receive at least one first portion of the electrical stimulation lead;
- a second plug base configured and arranged to be disposed around the first plug base and comprising a plurality of second grooves disposed around a circumference of the second plug base and configured and arranged to receive at least one second portion of the electrical stimulation lead including the plurality of terminals disposed along the proximal end of the electrical stimulation lead;
- a cover configured and arranged to be disposed on, and coupled to, the second plug base and to cover the plurality of second grooves;
- a cap configured and arranged to be disposed over the burr hole aperture and coupled to the first plug base; and
- an extension coupled to, and extending away from, the cover, the extension comprising a plurality of conductors, wherein the second plug base and the cover comprise a plurality of conductive elements configured and arranged to electrically couple the plurality of terminals of the electrical stimulation lead, when disposed in the second grooves, to the plurality of conductors of the extension.

13. The system of claim 12, wherein the proximal end of the electrical stimulation lead comprises a plurality of separable branches, each of the branches comprising at least one of the terminals.

14. The system of claim 13, wherein the first grooves of the first plug base and the separable branches of the proximal end of the electrical stimulation lead are equal in number.

15. The system of claim 13, wherein the second grooves of the second plug base and the separable branches of the proximal end of the electrical stimulation lead are equal in number.

16. The system of claim 12, wherein the conductive elements comprise a plurality of conductive contacts disposed in the second grooves of the second plug base.

17. The system of claim 12, wherein the conductive elements comprise a plurality of contacts disposed in the cover and configured and arranged to electrically couple to the terminals of the electrical stimulation lead disposed in the second grooves of the second plug base and a plurality of conductors extending along the cover from the plurality of contacts to the extension.

18. The system of claim 12, wherein the conductors of the extension form a single layer ribbon.

19. The system of claim 12 wherein a spacing between adjacent ones of the terminals of the electrical stimulation lead is equal to a spacing between adjacent ones of the conductive elements of the burr hole plug.

20. A method of implanting an electrical stimulation lead, the method comprising:
- providing the system of claim 12;
- inserting a distal end of the electrical stimulation lead into patient tissue;
- positioning at least one first portion of the proximal end of the electrical stimulation lead in at least one of the first grooves of the first plug base of the burr hole plug;
- positioning at least one second portion of the proximal end of the electrical stimulation lead in at least one of the second grooves of the second plug base of the burr hole plug, wherein each of the at least one second portion comprises at least one of the terminals of the electrical stimulation lead;
- attaching the cover to the second plug base; and
- attaching the cap to the first plug base.

* * * * *